United States Patent [19]

Gibson et al.

[11] Patent Number: 4,977,271
[45] Date of Patent: Dec. 11, 1990

[54] REISSERT COMPOUND OF BISBENZIMIDAZOLE

[75] Inventors: Harry W. Gibson; Yajnanarayana H. R. Jois, both of Blacksburg, Va.

[73] Assignee: Virginia Tech Intellectual Properties Inc., Blacksburg, Va.

[21] Appl. No.: 418,319

[22] Filed: Oct. 6, 1989

[51] Int. Cl.$^5$ .......................................... C07D 403/06
[52] U.S. Cl. ................................................... 548/328
[58] Field of Search ....................................... 548/328

[56] References Cited

U.S. PATENT DOCUMENTS 4,929,713  5/1990  Gibson et al. ...................... 528/230

OTHER PUBLICATIONS

Wang et al., Chemical Abstracts, vol. 52, entry 5387(f), (1958).

Primary Examiner—John M. Ford
Assistant Examiner—Lenora Miltenberger
Attorney, Agent, or Firm—Richard P. Fennelly; Louis A. Morris

[57] ABSTRACT

A Reissert compound of bisbenzimidazole can be formed by first reacting benzimidazole with an aliphatic diacid chloride to form bisbenzimidazole and then reacting the bisbenzimidazole with an aliphatic acid chloride and cyanide to form the Reissert compound thereof.

1 Claim, 1 Drawing Sheet

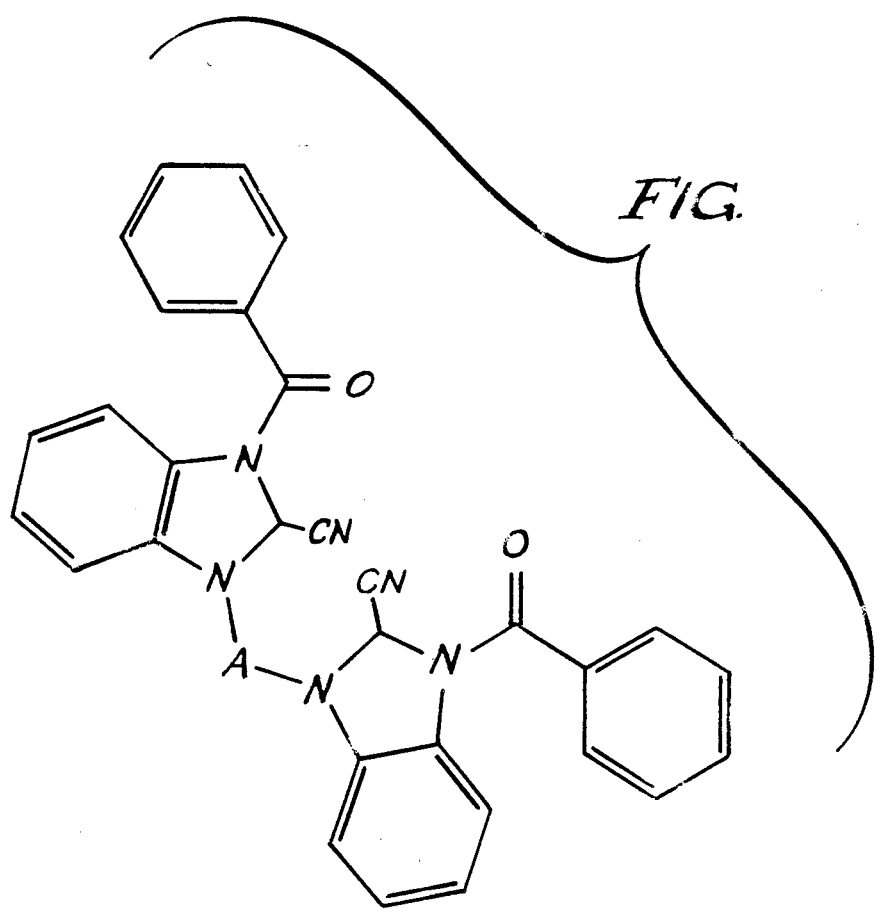
FIG.

REISSERT COMPOUND OF BISBENZIMIDAZOLE

BACKGROUND OF THE INVENTION

Because of the excellent mechanical and thermal properties imbued to polymers of benzimidazole (see Encycl. of Polymer. Sci. and Engineering, Second Edition, Vol. 7, pp. 639-665, 1987 and Encycl. of Polymer Sci. and Engineering, Second Edition, Vol. 11, pp. 572-601, 1988), it is desirable to incorporate this nucleus into these "Reissert compound polymers". However, only two examples of a Reissert-type compound from benzimidazole have been reported, and they were formed from chloroformates and not from acid chlorides (see J. Heterocyclic Chem. 1987, 24, 1349-1351). Attempts to use acid chlorides led to destruction of the benzimidazole nucleus (see J. Chem. Soc., Chem. Comm., 1984, 1245-1246). Thus, for the production of benzimidazole polymers by Reissert chemistry difunctionality was required as well as a means of producing Reissert compound moieties from acid chlorides. This invention relates to the discovery of methods for producing difunctional benzimidazole Reissert compounds.

DESCRIPTION OF THE INVENTION

The foregoing problem in regard to undesired bisbenzimidazole formation can be overcome by use of a two step process which yields a poly Reissert. The first step involves the reaction of benzimidazole to form bisbenzimidazole which is then reacted with acid chloride and cyanide to form the Reissert compound thereof.

The first step in the instant process involves reaction of benzimidazole with an aliphatic diacid chloride of the general formula ClC(O)RC(O)Cl, where R is alkylene (e.g., $C_4$-$C_6$ alkylene) to yield a bisbenzimidazole. This reaction can be conveniently performed under the following general conditions: Organic solvent (e.g., dimethyl formamide), base (e.g., triethylamine), temperatures of about 5° C. to 20 C., with mechanical stirring.

The bisbenzimidazole compound is then reacted with an aliphatic acid chloride and cyanide (e.g., trimethylsilyl cyanide) to yield the Reissert compound thereof having the structure

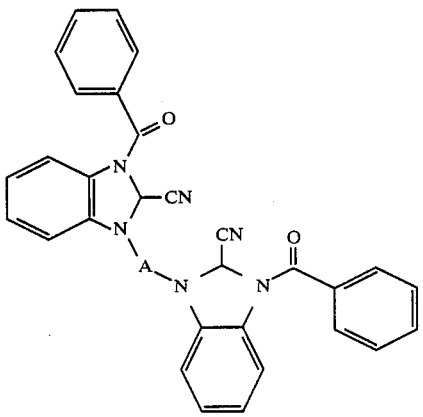

where A is C(O)RC(O) with R being alkylene. This reaction can be conducted in the same type of solvent used in the preceding step, at temperatures from 10° C. to 20° C. using amounts of the reagents which can range from 1 to 1.2 on a molar ratio basis.

The following Examples further illustrate the present invention.

EXAMPLE 1

This shows synthesis of the type of compound shown as (I) in the FIGURE, specifically, bis(benzimidazoyl-1,6-dicarbonyl hexane.

To a well stirred solution of benzimidazole (0.022 mole, 2.6 gm) and triethylamine (0.011 mole, 0.11 gm) in dimethylformamide (10 ml), adipoyl chloride (0.01 mole, 1.83 gm) in dichloromethane (10 ml) was added. The resulting reaction media was stirred at room temperature for twenty-four hours. The reaction mixture was poured into water and was stirred for three hours. An essentially quantitative yield of the product was obtained by filtering the solid from the liquid mixture and was washed with water, ethanol (2 and 10 ml portions), ether (2 and 25 ml portions) and was dried. The crude product was taken up in hot dimethylformamide (35 ml) and was precipitated by pouring into water (250 ml), was filtered, was crystallized from tetrahydrofuran, and was dried. The yield was 3.2 gm (93%).

Melting point: 250°-252° C. (dec)

IR (KBr): 3150-2900 (C-H), 1721 (N-CO), 1680, 1677, 1610, 1507 (aromatic), 1477, 1451, 1419, 1387, 1348, 1335, 1309, 1284, 1235, 1204, and 1165 cm$^{-1}$.

$^1$HNMR (DMSO-d) delta 8.96 (s, 2H, $C_{21}$-H), 8.25-8.15 (m, 2H, Ar-H), 7.78-7.74 (m, 2H, Ar-H), 7.45-7.35 (m, 4H, Ar-H), 3.3-3.2 (s, 4H $OCH_2$) and 1.95-1.80 (s, 4H $CH_2CH_2$).

EXAMPLE 2

Benzoyl chloride (0.0022 mole, 0.31 gm) was added to a well stirring suspension of bis(benzimidozoyl)1,6-dicarbonyl hexane from Example 1 (0.001 mole, 0.346 gm) in N-methylpyrrolidone (5 ml). Addition of trimethylsilyl cyanide (0.0022 mole, 0.3 ml) followed. The reaction mixture was stirred at room temperature for thirty-two hours and was quenched by pouring into 150 ml of water. The mixture was extracted with dichloromethane (3×50 ml). The organic layers were combined, washed with 8% hydrochloric acid (2×50 ml), aqueous saturated bicarbonate (2×50 ml), water (2×50 ml) and were dried. The crude product was treated with activated carbon (NORIT brand) and recrystalized from ethylacetate hexane. The yield was 350 gm (58%). The melting point Was 145-150° C.

IR (KBr): 2940, 2920 (C-H), 1660 (N-CO), 1595, 1485, 1370, 1360, 1345, 1275, and 1230 cm−1.

$^1$H NMR ($CDCl_3$): 8.3-6.1 (m, 20H, Ar-H), 3.1-2.4 (m, 4H, $COCH_2$), 2.2-1.4 (m, 4H, $CH_2CH_2$).

We claim:

1. A Reissert compound of bisbenzimidazole having the formula

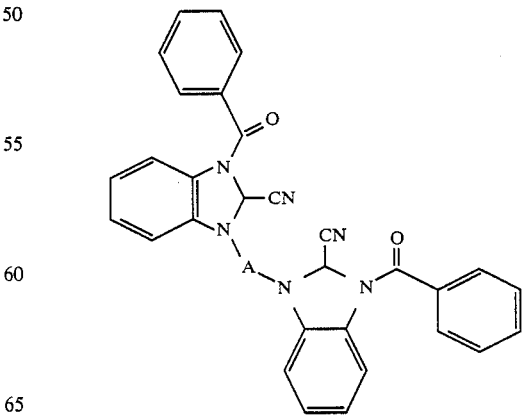

where A is C(O)RC(O) with R being alkylene.

* * * * *